US012653462B2

(12) United States Patent
Rijken et al.

(10) Patent No.: US 12,653,462 B2
(45) Date of Patent: Jun. 16, 2026

(54) ASSEMBLY FOR MOUNTING A SENSOR ON SKIN

(71) Applicant: XIVER MEMS FOUNDRY B.V., Eindhoven (NL)

(72) Inventors: Antonius Maria Rijken, Nuenen (NL); Johannes Antonius Van Rooij, Best (NL); Michiel Adriaan Cornelissen, Utrecht (NL); Franciscus Johannes Gerardus Hakkens, Eersel (NL); Edward Theodorus Maria Berben, Herten (NL)

(73) Assignee: XIVER MEMS FOUNDRY B.V., Eindhoven (NL)

( * ) Notice: Subject to any disclaimer, the term of this patent is extended or adjusted under 35 U.S.C. 154(b) by 716 days.

(21) Appl. No.: 17/608,850

(22) PCT Filed: May 14, 2020

(86) PCT No.: PCT/EP2020/063440
§ 371 (c)(1),
(2) Date: Nov. 4, 2021

(87) PCT Pub. No.: WO2020/229589
PCT Pub. Date: Nov. 19, 2020

(65) Prior Publication Data
US 2022/0313165 A1 Oct. 6, 2022

(30) Foreign Application Priority Data
May 14, 2019 (EP) ..................................... 19174286

(51) Int. Cl.
*A61B 5/00* (2006.01)

(52) U.S. Cl.
CPC ........ *A61B 5/6833* (2013.01); *A61B 5/68335* (2017.08); *A61B 5/6843* (2013.01); *A61B 2562/14* (2013.01)

(58) Field of Classification Search
CPC .......... A61B 2560/0412; A61B 8/4209; A61B 8/4236; A61B 5/6833; A61B 5/68335; A61B 5/6843; A61B 5/6825; A61B 5/681
See application file for complete search history.

(56) References Cited

U.S. PATENT DOCUMENTS 4,986,276 A     1/1991   Wright
2009/0030298 A1   1/2009   Matthews et al.
(Continued)

FOREIGN PATENT DOCUMENTS

EP      0316153 A1      5/1989
EP      1064052 A1      1/2001
(Continued)

OTHER PUBLICATIONS

International Search Report and Written Opinion for PCT/EP2020/063440, mailed Jul. 24, 2020, 9 pages.

*Primary Examiner* — Sana Sahand
(74) *Attorney, Agent, or Firm* — KDW Firm PLLC

(57) ABSTRACT

There is provided an assembly (500) for mounting a sensor (502) on the skin of a subject. The assembly comprises a part (504) configured to contact with a first surface (506) of a sensor unit (501) comprising the sensor when the sensor unit (501) is mounted in the assembly (500). The assembly (500) also comprises at least one resilient member (508) extending from an outer portion of the part (504) and configured to bias a second surface (510) of the sensor unit (501) against the skin of the subject when the sensor unit (501) is mounted in the assembly (500).

7 Claims, 3 Drawing Sheets

(a)                                  (b)

(56) References Cited

U.S. PATENT DOCUMENTS

| | | | |
|---|---|---|---|
| 2010/0022888 A1 | 1/2010 | George et al. | |
| 2010/0292589 A1* | 11/2010 | Goodman | A61B 5/02444 |
| | | | 600/500 |
| 2010/0305416 A1 | 12/2010 | Bédard et al. | |
| 2011/0279963 A1* | 11/2011 | Kumar | A61B 5/282 |
| | | | 156/60 |
| 2012/0197165 A1 | 8/2012 | Tanis et al. | |
| 2014/0257104 A1 | 9/2014 | Dunbar et al. | |
| 2015/0297137 A1* | 10/2015 | Welch | A61B 5/14535 |
| | | | 600/344 |
| 2016/0058380 A1* | 3/2016 | Lee | A61B 5/145 |
| | | | 600/365 |
| 2018/0049656 A1* | 2/2018 | Paulussen | A61B 5/02416 |
| 2019/0053759 A1* | 2/2019 | Cho | A61B 5/002 |

FOREIGN PATENT DOCUMENTS

| | | |
|---|---|---|
| EP | 3430993 A1 | 1/2019 |
| JP | H01221138 A | 9/1989 |
| JP | H0685600 U | 12/1994 |
| JP | 2018114105 A | 7/2018 |
| WO | 2005092177 A1 | 10/2005 |
| WO | 2011083409 A1 | 7/2011 |

* cited by examiner (a)            (b)

(a)            (b)

(a)                    (b)

(c)                    (d)

ASSEMBLY FOR MOUNTING A SENSOR ON SKIN

CROSS-REFERENCE TO PRIOR APPLICATIONS

This application is the U.S. National Phase application under 35 U.S.C. § 371 of International Application No. PCT/EP2020/063440, filed on May 14, 2020, which claims the benefit of European Patent Application No. 19174286.5, filed on May 14, 2019. These applications are hereby incorporated by reference herein.

FIELD OF THE INVENTION

The disclosure relates to an assembly for mounting a sensor on the skin of a subject.

BACKGROUND OF THE INVENTION

When a sensor is used for monitoring a subject (e.g. a blood vessel in the skin of the subject) over an extended period of time, the sensor needs to maintain good contact with the skin of the subject throughout the monitoring period in order for accurate measurements to be obtained. This is especially the case, for example, where the sensor is an ultrasound (US) transducer, which requires good acoustic contact to be maintained.

An existing technique for attaching a sensor to the skin of a subject is by attaching the sensor to the skin using an adhesive material. In such a technique, the sensor needs to be pushed onto the skin while being fixed into position in order to establish enough of a preload force to ensure the sensor has good physical contact with the skin, without air gaps. In some existing techniques, a liquid-based agent may be positioned between the sensor and the skin to prevent air gaps and improve the coupling. However, this presents a number of issues. For example, the liquid-based agent dries out over time and thus the thickness of a layer of that liquid-based agent located in between the sensor and the skin reduces over time. Moreover, the edges of adhesive materials used for attaching a sensor to the skin of a subject have a tendency to partially decouple from (or peel off) the skin over time.

As a result of these issues, the coupling between the skin and the sensor achieved in existing techniques weakens over time. Also, the initial preload force used to fix the sensor in place is not well-defined as it is operator (and skin condition) dependent according to the existing techniques. As such, skin may become irritated or injured over time if the initial preload force is too high, whereas the coupling between the sensor and the skin may be too weak if the initial preload force is too low. In a situation where the coupling between the sensor and the skin is weak, the sensor may at least partially detach from the skin. For example, the sensor may completely detach from the skin or there may be air gaps between the sensor and the skin. This can result in inaccurate measurements from the sensor.

US 2012/0197165 discloses an apparatus for mounting a US transducer in which a bias element (such as a spring) extends from a bottom portion of a housing to maintain a force on a US transducer module comprising the US transducer. The bias element is positioned centrally at the top surface of the US transducer module to allow the US transducer module to pivot. Thus, even in this apparatus, the same issues described above exist since the US transducer may be at least partially detached from the skin due to the pivoting action that is allowed and thus measurements obtained with the US transducer may be inaccurate.

SUMMARY OF THE INVENTION

As noted above, the limitations with existing techniques is that it is difficult to maintain sufficient coupling between the skin and the sensor for accurate measurements to be obtained from the sensor. It would thus be valuable to have an improvement aimed at addressing these limitations.

Therefore, according to a first aspect, there is provided an assembly for mounting a sensor on the skin of a subject. The assembly comprises a part configured to contact with a first surface of a sensor unit comprising the sensor when the sensor unit is mounted in the assembly. The assembly comprises at least one resilient member extending from an outer portion of the part and configured to bias a second surface of the sensor unit against the skin of the subject when the sensor unit is mounted in the assembly.

In some embodiments, the assembly may comprise at least one resilient member extending from the outer portion of the part on a first side of the assembly and at least one resilient member extending from the outer portion of the part on a second side of the assembly. In some embodiments, the second side may be opposite the first side.

In some embodiments, the at least one resilient member may extend around a perimeter of the outer portion of the part and may comprise at least one elongate aperture. In some embodiments, the resilient member may comprise a plurality of ribs extending around the perimeter of the outer portion of the part and defining the at least one elongate aperture. In some embodiments, at least one of the plurality of ribs may be coupled along a section of its length to the perimeter of the outer portion of the part. In some embodiments, at least one of the plurality of ribs may be configured to be attached to the skin of the subject or may be attached to at least one other rib that is configured to be attached to the skin of the subject. In some embodiments, the at least one elongate aperture may be configured to widen when the assembly is attached to the skin of the subject.

In some embodiments, the at least one resilient member may comprise at least one flexure element, at least one spring, or at least one pleated structure. In some embodiments, the at least one spring may comprise at least one helical spring.

In some embodiments, the assembly may comprise an adhesive member extending around a periphery of the assembly and configured to adhere the assembly to the skin of the subject. In some embodiments, the adhesive member may be configured to adhere the at least one resilient member to the skin of the subject. In some embodiments, the adhesive member may comprise a first protector covering an outer portion of the adhesive member around the perimeter of the adhesive member and/or a second protector covering an inner portion of the adhesive member. In some embodiments, at least the second protector may be removable.

In some embodiments, the assembly may comprise a sealing member configured to seal the assembly with respect to the skin of the subject.

In some embodiments, the at least one resilient member may be configured to bias the second surface of the sensor unit directly against the skin of the subject or indirectly against the skin of the subject via a coupling medium.

According to the aspects and embodiments described above, the limitations of existing techniques are addressed. In particular, according to the above-described aspects and embodiments, it is possible to ensure good contact and thus improved coupling of the sensor unit (and thus the sensor) with the skin of the subject for extended periods of time, while having more precise control on the preload force that is applied. This is achieved by the at least one resilient member extending from an outer portion of a part of the assembly, where the part is itself configured to contact with a surface of a sensor unit comprising the sensor, and the at least one resilient member being configured to bias another surface of the sensor unit against the skin of the subject. By ensuring that good contact and thus improved coupling is maintained over time, it is possible for more accurate measurements to be obtained by the sensor. There is thus provided an improved assembly for mounting a sensor on the skin of a subject.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which:

FIGS. 4(a), (b), (c) and (d) are schematic illustrations of an example assembly according to an embodiment.

DETAILED DESCRIPTION OF EMBODIMENTS

Figure 1:
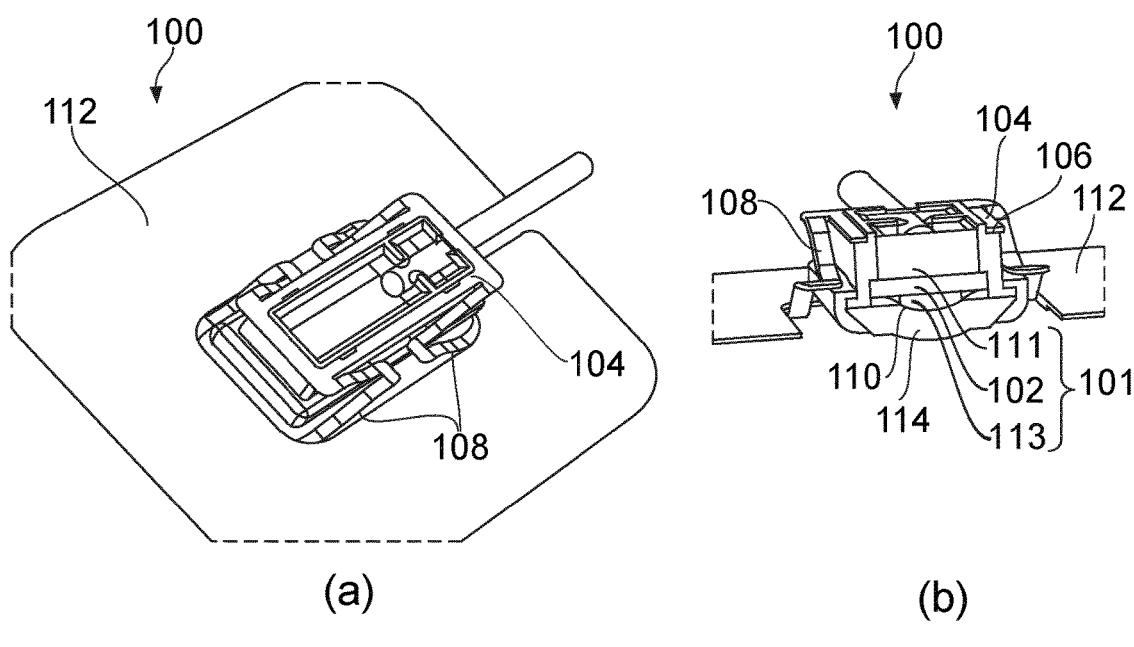
FIGS. 1(a) and (b) are schematic illustrations of an example assembly according to an embodiment.

As noted above, there is provided herein an improved assembly for mounting a sensor on the skin of a subject. The assembly comprises a part configured to contact with a first surface of a sensor unit comprising the sensor when the sensor unit is mounted in the assembly. The assembly also comprises at least one resilient (e.g. elastic) member extending from an outer portion of the part and configured to bias a second surface of the sensor unit against the skin of the subject when the sensor unit is mounted in the assembly. In this way, the assembly is pushed by the at least one resilient member onto the skin of the subject.

In some embodiments, the second surface of the sensor unit may be opposite the first surface of the sensor unit. For example, the second surface of the sensor unit may be (e.g. substantially) coplanar with the first surface of the sensor unit. In other embodiments, the second surface of the sensor unit may not be opposite the first surface of the sensor unit. For example, the second surface of the sensor unit may be (e.g. substantially) non-coplanar with the first surface of the sensor unit. In some embodiments, the second surface of the sensor unit may be adjacent to the first surface of the sensor unit. For example, the second surface of the sensor unit can be oblique or (e.g. substantially or approximately) perpendicular to the first surface of the sensor unit. In some embodiments, the first surface of the sensor unit referred to herein may be a first surface of the sensor itself and/or the second surface of the sensor unit referred to herein may be a second surface of the sensor itself In some embodiments, at least one resilient member may extend from the outer portion of the part that is configured to contact with a first surface of a sensor unit on a first side of the assembly and at least one resilient member may extend from the outer portion of the part that is configured to contact with a first surface of a sensor unit on a second side of the assembly. The second side of the assembly may be opposite the first side of the assembly. In some embodiments, at least one resilient member may extend around a perimeter of the part that is configured to contact with a first surface of a sensor unit.

The at least one resilient member referred to herein can be any member that is resilient (e.g. elastic). That is, the at least one resilient member may be any member that is configured to return back to (or resume) its original shape after being deformed, e.g. through stretching, compression, expansion, etc. The at least one resilient member referred to herein can take various forms. Examples of the at least one resilient member include, but are not limited to, at least one spring (e.g. at least one helical spring, and/or any other type of spring), at least one flexure element, at least one pleated (e.g. concertina) structure, or any other type of resilient member, or any combination of resilient members, suitable for biasing the second surface of the sensor unit against the skin of the subject when the sensor unit is mounted in the assembly.

In some embodiments, the at least one resilient member may be configured to bias the second surface of the sensor unit directly against the skin of the subject. In other embodiments, the at least one resilient member may be configured to bias the second surface of the sensor unit indirectly against the skin of the subject, such as via a coupling medium (e.g. an acoustic coupling medium). Examples of a coupling medium include, but are not limited to, a gel, a gel pad, a water absorbing polymer, or any other coupling medium, or any combination of coupling mediums. The coupling medium can improve coupling between the sensor unit and the skin of the subject.

As mentioned earlier, the sensor unit referred to herein comprises the sensor. In some embodiments, the sensor unit may comprise only the sensor. In other embodiments, the sensor unit may also comprise one or more additional components. The sensor and/or the one or more additional components may be coupled or attached (such as bonded, e.g. glued) together. In some embodiments, the one or more additional components can comprise a backing material, a lens and/or one or more other additional components.

In embodiments where the sensor unit comprises a backing material, the backing material can be configured to be positioned on a first surface of the sensor. The first surface of the sensor is the surface of the sensor that faces away from the skin of the subject when the sensor unit is mounted in the assembly and the assembly is in use. In some embodiments, the backing material may be coupled or attached (such as bonded, e.g. glued) to the sensor. The backing material may be configured to keep the sensor cool.

In embodiments where the sensor unit comprises a lens, the lens can be configured to be positioned on a second surface of the sensor. The second surface of the sensor is the surface of the sensor that faces the skin of the subject when the sensor unit is mounted in the assembly and the assembly is in use. The second surface of the sensor can be opposite the first surface of the sensor. Thus, the lens can be configured to be positioned between the sensor and the skin when the sensor unit is mounted in the assembly and the assembly is in use. In some embodiments, the lens may be coupled or attached (such as bonded, e.g. glued) to the sensor. In some embodiments, the second surface of the sensor unit can be the surface of the lens that is configured to face the skin of the subject when the sensor unit is mounted in the assembly and the assembly is in use. In embodiments involving a coupling medium, the coupling medium may be positioned on the side of the lens that is configured to face the skin of the subject when the sensor unit is mounted in the assembly and the assembly is in use. That is, in some embodiments, the coupling medium may be positioned between the lens and the skin when the sensor unit is mounted in the assembly and the assembly is in use.

The sensor referred to herein can, for example, comprise one or more physiological characteristic sensors, such as one or more heart rate sensors, one or more blood pressure sensors, or any other physiological characteristic sensor, or any combination of physiological characteristic sensors. In some embodiments, the sensor may comprise one or more ultrasound sensor (e.g. one or more ultrasound transducers), one or more optical sensors (e.g. one or more optical heart rate sensors), or any other type of sensor, or any combination or types of sensor. The sensor referred to herein can be any sensor that is configured to be worn on (e.g. fixed to, such as by pushing against) the skin of the subject. Thus, the sensor referred to herein can be a wearable sensor. In the same way, the sensor unit can be a wearable sensor unit. The sensor can be a sensor used to monitor a subject, e.g. over an extended period of time.

In some embodiments, the assembly may comprise a sealing member (e.g. a seal ring). The sealing member can be configured to seal the assembly with respect to the skin of the subject. For example, in embodiments involving a coupling medium, the sealing member can be configured to seal the second surface of the sensor unit and the coupling medium with respect to the skin of the subject. That is, the sealing member can be configured to seal the coupling medium between the second surface of the sensor unit and the skin of the subject. This prevents the coupling medium being in direct contact with air and avoids evaporation. In this way, dehydration of the coupling medium is prevented and coupling of the sensor unit (and thus the sensor) can be maintained for longer periods of time, e.g. up to 7 days without noticeable deterioration. In the same way the at least one resilient member is configured to bias the second surface of the sensor unit against the skin of the subject when the sensor unit is mounted in the assembly, the at least one resilient member can also be configured to bias the sealing member against the skin of the subject when the sensor unit is mounted in the assembly. Thus, the sealing member can be pressed against the skin with a well-defined force, which prevents irritation. In some embodiments, the sealing member can be formed from a hard material, such as a hard polymer. This can limit the friction between the sealing member and the skin to avoid skin irritation.

In some embodiments, the assembly may comprise an adhesive member (e.g. a plaster). The adhesive member can extend around a periphery of the assembly, e.g. at least a part of the periphery or the entire periphery of the assembly. The adhesive member may be configured to adhere (or fix) the assembly to the skin of the subject. In some embodiments, the adhesive member may be configured to adhere (or fix) the at least one resilient member to the skin of the subject. In some embodiments, the adhesive member can comprise a first protector (e.g. liner) covering an outer (or edge) portion of the adhesive member around the perimeter of the adhesive member and/or a second protector (e.g. liner) covering an inner (or local) portion of the adhesive member. In some embodiments, the first protector and/or the second protector may be removable. For example, at least the second protector may be removable according to some embodiments.

By only removing the second protector, the assembly comprising the adhesive member can slide over the skin of the subject by way of the first protector to aid in positioning the assembly. The outer portion of the adhesive member covered by the first protector is prevented from making contact with and adhering to the skin of the subject (and then causing wrinkling of the adhesive member), which makes repositioning of the assembly comprising the adhesive member easier. This can be beneficial in view of uneven anatomy, such as in the case of a concave part of the anatomy like in the neck above the carotid artery. Once a correct position of the assembly on the skin of the subject is reached, the assembly can be pressed down and the inner portion of the adhesive member from which the second protector is removed can adhere (or fix) to the skin. The first protector may then be removed or, alternatively, can be left in place. In many applications it can be useful to position a sensor by imaging to determine the correct position, e.g. above or with respect to an artery. Thus, in the manner described, a physician can easily move the assembly while imaging the skin until the correct position is reached, at which point the assembly can be adhered (or fixed) in place.

FIGS. 1(a) and (b) illustrate an example assembly 100 for mounting a sensor 102 on the skin of a subject according to an embodiment. As mentioned earlier and as illustrated in FIGS. 1(a) and (b), the assembly 100 comprises a part 104 configured to contact with a first surface 106 of a sensor unit 101 comprising the sensor 102 when the sensor unit 101 is mounted in the assembly 100. As also mentioned earlier and as illustrated in FIGS. 1(a) and (b), the assembly 100 further comprises at least one resilient member 108 extending from an outer portion of the part 104. The at least one resilient member 108 is configured to bias a second surface 110 of the sensor unit 101 against the skin of the subject when the sensor unit 101 is mounted in the assembly 100. In the example embodiment illustrated in FIGS. 1(a) and (b), the second surface 110 is opposite (e.g. coplanar or substantially coplanar with) the first surface 106.

In some embodiments, such as that illustrated in FIGS. 1(a) and (b), at least one resilient member 108 may extend from the outer portion of the part 104 on a first side of the assembly 100 and at least one resilient member 108 may extend from the outer portion of the part 104 on a second side of the assembly 100. The second side of the assembly 100 may be opposite the first side of the assembly 100.

In the example embodiment illustrated in FIGS. 1(a) and (b), the at least one resilient member 108 comprises at least one flexure element (e.g. at least one flexure structure or at least one flexure member). The at least one flexure element is defined as at least one element (e.g. at least one structure or at least one member) that is flexed (or bent). The at least one element is flexed (or bent) such that the at least one element can bias the second surface 110 of the sensor unit 101 against the skin of the subject when the sensor unit 101 is mounted in the assembly 100.

In some embodiments, such as that illustrated in FIGS. 1(a) and (b), at least one flexure element may be a V-shaped or U-shaped flexure element. That is, in some embodiments, at least one flexure element may be an elongate element that is flexed (or bent) to form a point or an arc. Thus, in some embodiments, at least one flexure element may comprise two elongate members extending from a point or an arc. In some embodiments, the two elongate members may extend parallel to each other from the point or arc. In other embodiments, the two elongate members may extend away from each other from a point or an arc. In some embodiments, without the sensor unit 101 mounted in the assembly 100, the two elongate members may lie (e.g. substantially) in the same plane (e.g. side-by-side). This can be referred to as the resting position of the at least one flexure element. In these embodiments, when the sensor unit 101 is mounted in the assembly 100, the two elongate members may be pulled apart from one another at their ends distal to the point or arc from which the two elongate members extend. Thus, in some embodiments, at least one flexure element can be stretched (e.g. from its resting position) to bias the second surface 110 of the sensor unit 101 against the skin of the subject when the sensor unit 101 is mounted in the assembly 100. In these embodiments, elastic distortion can provide a preload force.

Although the assembly 100 is illustrated as comprising two pairs of flexure elements according to the example embodiment illustrated in FIGS. 1(*a*) and (*b*), it will be understood that the assembly 100 may comprise any other number of flexure elements suitable for biasing the second surface 110 of the sensor unit 101 against the skin of the subject when the sensor unit 101 is mounted in the assembly 100. In some embodiments where at least one resilient member 108 extends from the outer portion of the part 104 on a first side of the assembly 100 and at least one resilient member 108 extends from the outer portion of the part 104 on a second side of the assembly 100, as illustrated in FIGS. 1(*a*) and (*b*), at least a first pair of flexure elements may extend from the outer portion of the part 104 on the first side of the assembly 100 and at least a second pair flexure elements may extend from the outer portion of the part 104 on the second side of the assembly 100.

As illustrated in FIGS. 1(*a*) and (*b*), in some embodiments, at least one flexure element may be coupled to (or joined with) the part 104 that is configured to contact with the first surface 106 of the sensor unit 101 when the sensor unit 101 is mounted in the assembly 100. In some embodiments, the part 104 that is configured to contact with the first surface 106 of the sensor unit 101 when the sensor unit 101 is mounted in the assembly 100 may extend around at least a portion of the perimeter of the assembly 100. Thus, in some embodiments, the part 104 may be configured to extend across the first surface 106 of the sensor unit 101 when the sensor unit 101 is mounted in the assembly 100. In embodiments where the assembly 100 comprises more than one flexure element, at least one flexure element may be coupled to (or joined with) at least one other flexure element by the part 104, e.g. across the first surface 106 of the sensor unit 101 when the sensor unit 101 is mounted in the assembly 100.

Although not illustrated in FIGS. 1(*a*) and (*b*), in some embodiments, the at least one resilient member 108 may be configured to bias the second surface 110 of the sensor unit 101 directly against the skin of the subject. In other embodiments, such as that illustrated in FIGS. 1(*a*) and (*b*), the at least one resilient member 108 is configured to bias the second surface 110 of the sensor unit 101 indirectly against the skin of the subject via a coupling medium 114, such as any of those mentioned earlier.

As mentioned earlier and as illustrated in FIGS. 1(*a*) and (*b*), in some embodiments, the sensor unit 101 may comprise one or more additional components, such as a backing material 111 (as described earlier), a lens 113 (as described earlier) and/or one or more other additional components. However, it will be understood that in other embodiments, the sensor unit 101 may comprise only the sensor 102.

In the example embodiment illustrated in FIGS. 1(*a*) and (*b*), the assembly 100 comprises an adhesive member 112. The adhesive member 112 may extend around a periphery of the assembly 100, e.g. at least a part of the periphery or the entire periphery of the assembly 100. The adhesive member 112 may be configured to adhere (or fix) the assembly 100 to the skin of the subject. More specifically, in the example embodiment illustrated in FIGS. 1(*a*) and (*b*), the adhesive member 112 can be configured to adhere (or fix) the at least one resilient member 108 to the skin of the subject. For example, where the at least one resilient member 108 comprises at least one flexure element comprising two elongate members extending from a point or an arc, the adhesive member 112 can be configured to adhere one of the elongate members at its end distal to the point or arc from which it extends to adhere the elongate member to the skin of the subject. This holds the elongate member against the skin of the subject when the at least one flexure element is stretched (e.g. from its resting position) to bias the second surface 110 of the sensor unit 101 against the skin of the subject when the sensor unit 101 is mounted in the assembly 100. Thus, adhering (or fixing) the assembly 100 to the skin of the subject by bringing the adhesive member 112 toward the skin of the subject can cause the at least one resilient member 108 to be preloaded.

Although not illustrated in FIGS. 1(*a*) and (*b*), the adhesive member 112 can comprise a first protector (as described earlier) covering an outer portion of the adhesive member 112 around the perimeter of the adhesive member 112. Alternatively or in addition, the adhesive member 112 may comprise a second protector (as described earlier) covering an inner portion of the adhesive member 112. In some embodiments, the first protector and/or the second protector may be removable. For example, at least the second protector may be removable according to some embodiments.

Figure 2:
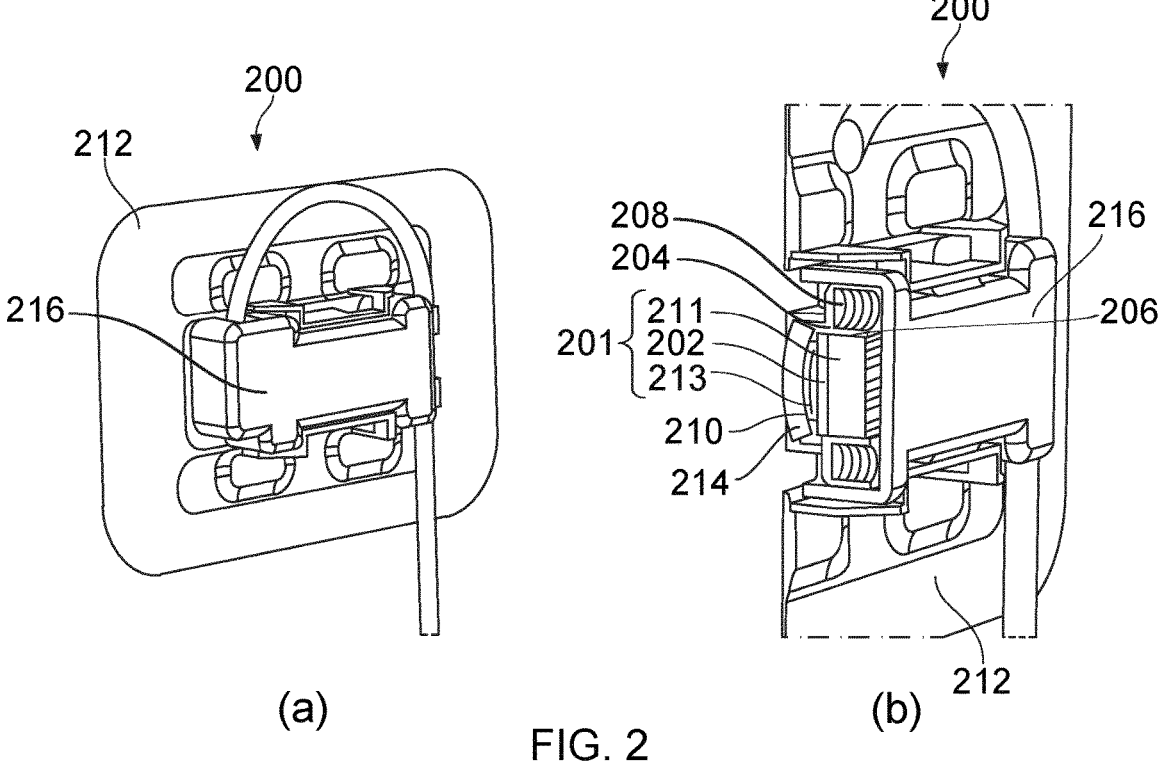
FIGS. 2(a) and (b) are schematic illustrations of an example assembly according to an embodiment.

FIGS. 2(*a*) and (*b*) illustrate an example assembly 200 for mounting a sensor 202 on the skin of a subject according to an embodiment. As mentioned earlier and as illustrated in FIGS. 2(*a*) and (*b*), the assembly 200 comprises a part 204 configured to contact with a first surface 206 of a sensor unit 201 comprising the sensor 202 when the sensor unit 201 is mounted in the assembly 200. As also mentioned earlier and as illustrated in FIGS. 2(*a*) and (*b*), the assembly 200 further comprises at least one resilient member 208 extending from an outer portion of the part 204. The at least one resilient member 208 is configured to bias a second surface 210 of the sensor unit 201 against the skin of the subject when the sensor unit 201 is mounted in the assembly 200. In the example embodiment illustrated in FIGS. 2(*a*) and (*b*), the second surface 210 of the sensor unit 201 is not be opposite the first surface 206 of the sensor unit 201. Instead, as described earlier, the second surface 210 of the sensor unit 201 is (e.g. substantially) non-coplanar with the first surface 206 of the sensor unit 201.

In some embodiments, such as that illustrated in FIGS. 2(*a*) and (*b*), at least one resilient member 208 may extend from the outer portion of the part 204 on a first side of the assembly 200 and at least one resilient member 208 may extend from the outer portion of the part 204 on a second side of the assembly 200. The second side of the assembly 200 may be opposite the first side of the assembly 200.

In the example embodiment illustrated in FIGS. 2(*a*) and (*b*), the at least one resilient member 208 comprises at least one spring. The at least one spring may, for example, comprise at least one helical spring. The at least one spring is held in a compressed state, such that the at least one spring exerts a force that biases the second surface 210 of the sensor unit 201 against the skin of the subject when the sensor unit 201 is mounted in the assembly 200. In some embodiments, the at least one spring may be attached (e.g. fixed) to the sensor unit 201 in use and/or may be in contact with any one or more components (e.g. the sensor 202 and/or any other components of the sensor unit 201).

Although the assembly 200 is illustrated as comprising two springs according to the example embodiment illustrated in FIGS. 2(*a*) and (*b*), it will be understood that the assembly 200 may comprise any other number of springs suitable for biasing the second surface 210 of the sensor unit 201 against the skin of the subject when the sensor unit 201 is mounted in the assembly 200.

Although not illustrated in FIGS. 2(*a*) and (*b*), in some embodiments, the at least one resilient member 208 may be configured to bias the second surface 210 of the sensor unit 201 directly against the skin of the subject. In other embodiments, such as that illustrated in FIGS. 2(*a*) and (*b*), the at least one resilient member 208 is configured to bias the second surface 210 of the sensor unit 201 indirectly against the skin of the subject via a coupling medium 214, such as any of those mentioned earlier.

As mentioned earlier and as illustrated in FIGS. 2(*a*) and (*b*), in some embodiments, the sensor unit 201 may comprise one or more additional components, such as a backing material 211 (as described earlier), a lens 213 (as described earlier) and/or one or more other additional components. However, it will be understood that in other embodiments, the sensor unit 201 may comprise only the sensor 202.

In the example embodiment illustrated in FIGS. 2(*a*) and (*b*), the assembly 200 comprises an adhesive member 212. The adhesive member 212 may extend around a periphery of the assembly 200, e.g. at least a part of the periphery or the entire periphery of the assembly 200. The adhesive member 212 may be configured to adhere (or fix) the assembly 200 to the skin of the subject.

Although not illustrated in FIGS. 2(*a*) and (*b*), the adhesive member 212 can comprise a first protector (as described earlier) covering an outer portion of the adhesive member 212 around the perimeter of the adhesive member 212. Alternatively or in addition, the adhesive member 212 may comprise a second protector (as described earlier) covering an inner portion of the adhesive member 212. In some embodiments, the first protector and/or the second protector may be removable. For example, at least the second protector may be removable according to some embodiments.

In some embodiments, such as that illustrated in FIGS. 2(*a*) and (*b*), the assembly 200 may comprise a housing 216. The housing 216 can be configured to house (e.g. cover or contain) the sensor unit 201 and the part 204 that is configured to contact with a first surface 206 of the sensor unit 201 when the sensor unit 201 is mounted in the assembly 200. In embodiments involving a coupling medium 214, the housing 216 can also be configured to house (e.g. cover or contain) the coupling medium 214. In embodiments involving the housing 216, the at least one spring may be held in the compressed state mentioned earlier between an inner surface of the housing 216 and the part 204 that is configured to contact with the first surface 206 of the sensor unit 201 comprising the sensor 202 when the sensor unit 201 is mounted in the assembly 200.

Figures 3, 4:
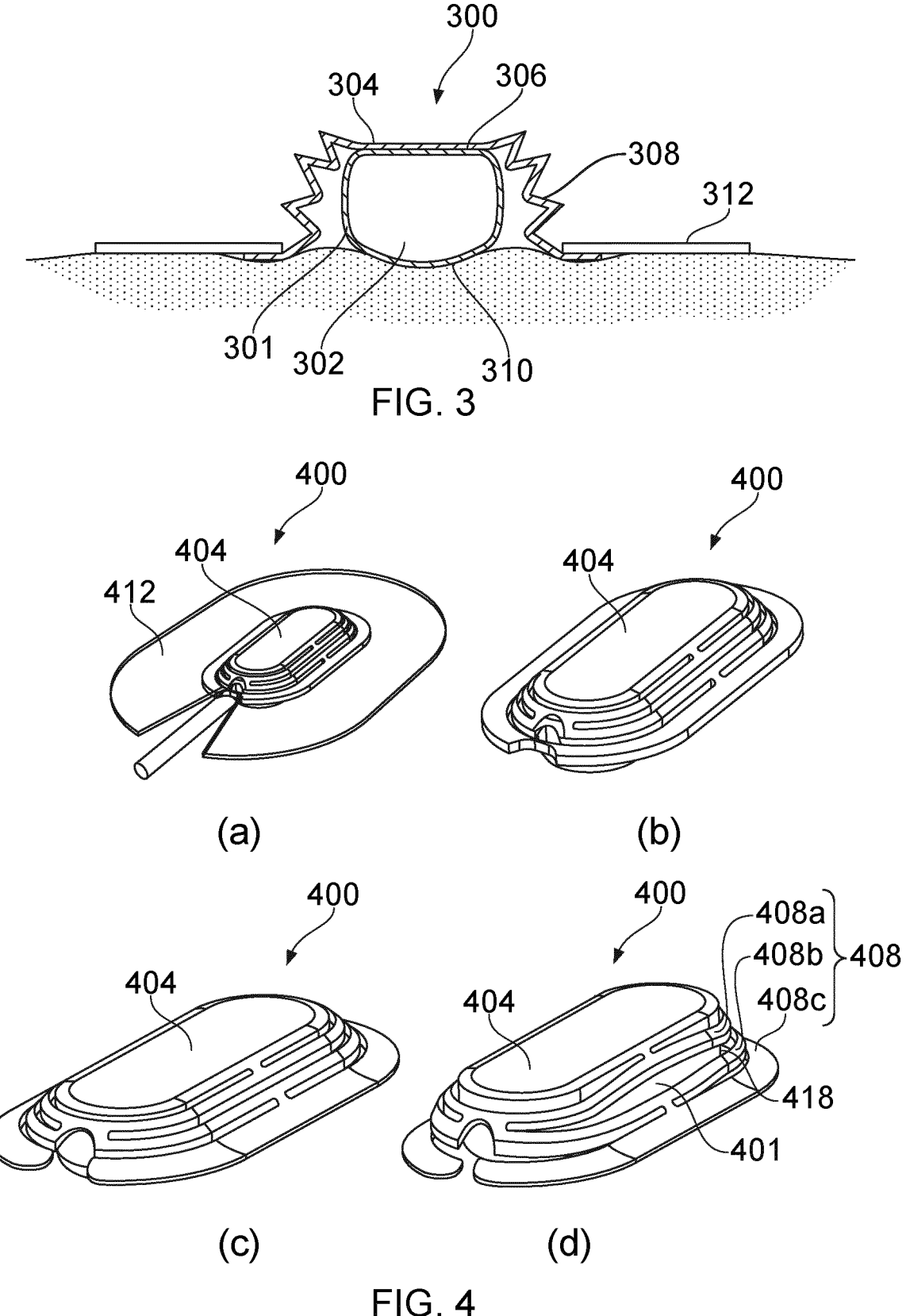
FIG. 3 is a schematic illustration of an example assembly according to an embodiment.

FIG. 3 illustrates an example assembly 300 for mounting a sensor 302 on the skin of a subject according to an embodiment. As mentioned earlier and as illustrated in FIG. 3, the assembly 300 comprises a part 304 configured to contact with a first surface 306 of a sensor unit 301 comprising the sensor 302 when the sensor unit 301 is mounted in the assembly 300. As also mentioned earlier and as illustrated in FIG. 3, the assembly 300 further comprises at least one resilient member 308 extending from an outer portion of the part 304. The at least one resilient member 308 is configured to bias a second surface 310 of the sensor unit 301 against the skin of the subject when the sensor unit 301 is mounted in the assembly 300. In the example embodiment illustrated in FIG. 3, the second surface 310 is opposite (e.g. coplanar or substantially coplanar with) the first surface 306.

In some embodiments, such as that illustrated in FIG. 3, at least one resilient member 308 may extend from the outer portion of the part 304 on a first side of the assembly 300 and at least one resilient member 308 may extend from the outer portion of the part 304 on a second side of the assembly 300. In some embodiments, the second side of the assembly 300 may be opposite the first side of the assembly 300. In some embodiments, at least one resilient member 308 may extend around a perimeter of the part 304.

In the example embodiment illustrated in FIG. 3, the at least one resilient member 308 comprises at least one pleated (e.g. concertina) structure. The at least one pleated structure comprises a plurality of pleats. The at least one pleated structure is configured to move between a first (relaxed or resting) position in which the plurality of pleats are contracted and a second position in which the plurality of pleats are expanded (or stretched out). In the first position, where the plurality of pleats are contracted, the plurality of pleats are drawn together. The plurality of pleats are contracted without the sensor unit 301 mounted in the assembly 300. In the second position, where the plurality of pleats are expanded, the plurality of pleats are pulled apart. The plurality of pleats are expanded when the sensor unit 301 is mounted in the assembly 300. When the plurality of pleats are expanded, the plurality of pleats exert a force (as they try to return to the first position from the second position), which holds the elongate member against the skin of the subject to bias the second surface 310 of the sensor unit 301 against the skin of the subject when the sensor unit 301 is mounted in the assembly 100.

Although not illustrated in FIG. 3, in some embodiments, the at least one resilient member 308 may be configured to bias the second surface 310 of the sensor unit 301 indirectly against the skin of the subject via a coupling medium, such as any of those mentioned earlier. In other embodiments such as that illustrated in FIG. 3, the at least one resilient member 308 is configured to bias the second surface 310 of the sensor unit 301 directly against the skin of the subject.

As mentioned earlier and as illustrated in FIG. 3, in some embodiments, the sensor unit 301 may comprise only the sensor 302. However, it will be understood that in other embodiments, the sensor unit 301 may comprise one or more additional components, such as a backing material (as described earlier), a lens (as described earlier) and/or one or more other additional components.

In the example embodiment illustrated in FIG. 3, the assembly 300 comprises an adhesive member 312. The adhesive member 312 may extend around a periphery of the assembly 300, e.g. at least a part of the periphery or the entire periphery of the assembly 300. The adhesive member 312 may be configured to adhere (or fix) the assembly 300 to the skin of the subject. More specifically, in the example embodiment illustrated in FIG. 3, the adhesive member 312 can be configured to adhere (or fix) the at least one resilient member 308 to the skin of the subject. Where the at least one resilient member 308 comprises at least one pleated structure comprising a plurality of pleats, adhering (or fixing) the at least one resilient member 308 to the skin of the subject by bringing the adhesive member 312 toward the skin of the subject can cause the at least one pleated structure to move between the first position in which the plurality of pleats are contracted to the second position in which the plurality of pleats are expanded.

Although not illustrated in FIG. 3, the adhesive member 312 can comprise a first protector (as described earlier) covering an outer portion of the adhesive member 312 around the perimeter of the adhesive member 312. Alternatively or in addition, the adhesive member 312 may comprise a second protector (as described earlier) covering an inner portion of the adhesive member 312. In some embodiments, the first protector and/or the second protector may be removable. For example, at least the second protector may be removable according to some embodiments.

FIGS. 4(*a*), (*b*), (*c*) and (*d*) illustrate an example assembly 400 for mounting a sensor (not illustrated) on the skin of a subject according to an embodiment. As mentioned earlier and as illustrated in FIGS. 4(*a*), (*b*), (*c*) and (*d*), the assembly 400 comprises a part 404, which is configured to contact with a first surface of a sensor unit 401 comprising the sensor when the sensor unit 401 is mounted in the assembly 400. As also mentioned earlier and as illustrated in FIGS. 4(*a*), (*b*), (*c*) and (*d*), the assembly 400 further comprises at least one resilient member 408 extending from an outer portion of the part 404. The at least one resilient member 408 is configured to bias a second surface of the sensor unit 401 against the skin of the subject when the sensor unit 401 is mounted in the assembly 400. In the example embodiment illustrated in FIGS. 4(*a*), (*b*), (*c*) and (*d*), the second surface is opposite (e.g. coplanar or substantially coplanar with) the first surface.

In some embodiments, such as that illustrated in FIGS. 4(*a*), (*b*), (*c*) and (*d*), at least one resilient member 408 may extend from the outer portion of the part 404 on a first side of the assembly 400 and at least one resilient member 408 may extend from the outer portion of the part 404 on a second side of the assembly 400. In some embodiments, the second side of the assembly 400 may be opposite the first side of the assembly 400. In the example embodiment illustrated in FIGS. 4(*a*), (*b*), (*c*) and (*d*), the at least one resilient member 408 extends around a perimeter of the outer portion of the part 404 and comprises at least one elongate aperture 418.

In more detail, as illustrated in FIGS. 4(*a*), (*b*), (*c*) and (*d*), the resilient member 408 may comprise a plurality of ribs 408*a*, 408*b*, 408*c* extending around the perimeter of the outer portion of the part 404 and defining the at least one elongate aperture 418. As illustrated in FIG. 4(*d*), the at least one elongate aperture 418 can be configured to widen when the assembly 400 is attached to the skin of the subject. In some embodiments, such as that illustrated in FIGS. 4(*a*), (*b*), (*c*) and (*d*), at least one of the plurality of ribs 408*a* may be coupled (or joined) along a section of its length to the perimeter of the outer portion of the part 404. Thus, at least one of the plurality of ribs 408*a* and the outer portion of the part 404 may form an H-shape (or an H-shaped flexure). In some embodiments, at least one of the plurality of ribs 408*b* may be configured to be attached to the skin of the subject. In other embodiments, such as that illustrated in FIGS. 4(*a*), (*b*), (*c*) and (*d*), at least one of the plurality of ribs 408*b* can be configured to be attached (e.g. coupled or joined) to at least one other rib 408*c* that is configured to be attached to the skin of the subject. Thus, at least one of the plurality of ribs 408*b* and at least one other rib 408*c* may form an H-shape (or an H-shaped flexure). Although the example embodiment of FIGS. 4(*a*), (*b*), (*c*) and (*d*) illustrates a resilient member 408 comprising three ribs 408*a*, 408*b*, 408*c*, it will be understood that the resilient member 408 may comprise any other number of ribs.

Although not illustrated in FIGS. 4(*a*), (*b*), (*c*) and (*d*), in some embodiments, the at least one resilient member 408 may be configured to bias the second surface 410 of the sensor unit 401 indirectly against the skin of the subject via a coupling medium, such as any of those mentioned earlier. Although also not illustrated in FIGS. 4(*a*), (*b*), (*c*) and (*d*), in other embodiments, the at least one resilient member 408 may be configured to bias the second surface 410 of the sensor unit 401 directly against the skin of the subject.

As mentioned earlier, in some embodiments, the sensor unit 401 may comprise one or more additional components, such as a backing material (as described earlier), a lens (as described earlier) and/or one or more other additional components. However, it will be understood that in other embodiments, the sensor unit 401 may comprise only the sensor.

In the example embodiment illustrated in FIGS. 4(*a*), (*b*), (*c*) and (*d*), the assembly 400 comprises an adhesive member 412. The adhesive member 412 may extend around a periphery of the assembly 400, e.g. at least a part of the periphery or the entire periphery of the assembly 400. The adhesive member 412 may be configured to adhere (or fix) the assembly 400 to the skin of the subject. More specifically, in the example embodiment illustrated in FIGS. 4(*a*), (*b*), (*c*) and (*d*), the adhesive member 412 can be configured to adhere (or fix) the at least one resilient member 408 to the skin of the subject.

Although not illustrated in FIGS. 4(*a*), (*b*), (*c*) and (*d*), the adhesive member 412 can comprise a first protector (as described earlier) covering an outer portion of the adhesive member 412 around the perimeter of the adhesive member 412. Alternatively or in addition, the adhesive member 412 may comprise a second protector (as described earlier) covering an inner portion of the adhesive member 412. In some embodiments, the first protector and/or the second protector may be removable. For example, at least the second protector may be removable according to some embodiments.

Figure 5:
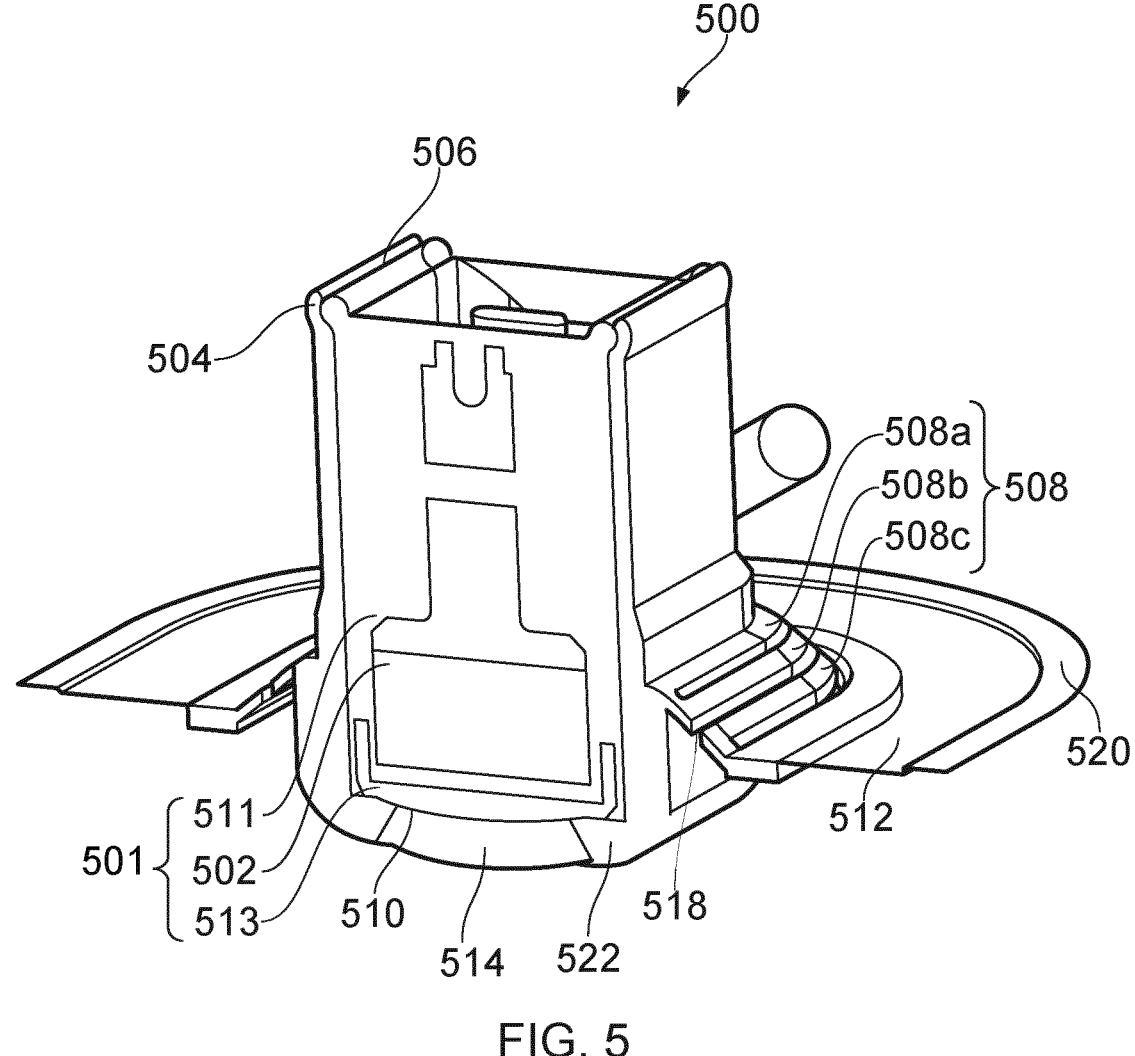
FIG. 5 is a schematic illustration of an example assembly according to an embodiment.

FIG. 5 illustrates an example assembly 500 for mounting a sensor 502 on the skin of a subject according to an embodiment. As mentioned earlier and as illustrated in FIG. 5, the assembly 500 comprises a part 504 configured to contact with a first surface 506 of a sensor unit 501 comprising the sensor 502 when the sensor unit 501 is mounted in the assembly 500. As also mentioned earlier and as illustrated in FIG. 5, the assembly 500 further comprises at least one resilient member 508 extending from an outer portion of the part 504. The at least one resilient member 508 is configured to bias a second surface 510 of the sensor unit 501 against the skin of the subject when the sensor unit 501 is mounted in the assembly 500. In the example embodiment illustrated in FIG. 5, the second surface 510 of the sensor unit 501 is not be opposite the first surface 506 of the sensor unit 501. Instead, as described earlier, the second surface 510 of the sensor unit 501 is (e.g. substantially) non-coplanar with the first surface 506 of the sensor unit 501.

In some embodiments, such as that illustrated in FIG. 5, at least one resilient member 508 may extend from the outer portion of the part 504 on a first side of the assembly 500 and at least one resilient member 508 may extend from the outer portion of the part 504 on a second side of the assembly 500. In some embodiments, the second side of the assembly 500 may be opposite the first side of the assembly 500. In the example embodiment illustrated in FIG. 5, the at least one resilient member 508 extends around a perimeter of the outer portion of the part 504 and comprises at least one elongate aperture 518.

In more detail, as illustrated in FIG. 5, the resilient member 508 may comprise a plurality of ribs 508*a*, 508*b*, 508c extending around the perimeter of the outer portion of the part 504 and defining the at least one elongate aperture 518. The at least one elongate aperture 518 can be configured to widen when the assembly 500 is attached to the skin of the subject. In some embodiments, such as that illustrated in FIG. 5, at least one of the plurality of ribs 508a may be coupled (or joined) along a section of its length to the perimeter of the outer portion of the part 504. Thus, at least one of the plurality of ribs 508a and the outer portion of the part 504 may form an H-shape (or an H-shaped flexure). In some embodiments, at least one of the plurality of ribs 508b may be configured to be attached to the skin of the subject. In other embodiments, such as that illustrated in FIG. 5, at least one of the plurality of ribs 508b can be configured to be attached (e.g. coupled or joined) to at least one other rib 508c that is configured to be attached to the skin of the subject. Thus, at least one of the plurality of ribs 508b and at least one other rib 508c may form an H-shape (or an H-shaped flexure). Although the example embodiment of FIG. 5 illustrates a resilient member 508 comprising three ribs 508a, 508b, 508c, it will be understood that the resilient member 508 may comprise any other number of ribs.

Although also not illustrated in FIG. 5, in some embodiments, the at least one resilient member 508 may be configured to bias the second surface 510 of the sensor unit 501 directly against the skin of the subject. In other embodiments, such as that illustrated in FIG. 5, the at least one resilient member 508 is configured to bias the second surface 510 of the sensor unit 501 indirectly against the skin of the subject via a coupling medium 514, such as any of those mentioned earlier.

As mentioned earlier and as illustrated in FIG. 5, in some embodiments, the sensor unit 501 may comprise one or more additional components, such as a backing material 511 (as described earlier), a lens 513 (as described earlier) and/or one or more other additional components. However, it will be understood that in other embodiments, the sensor unit 501 may comprise only the sensor 501.

In some embodiments, such as that illustrated in FIG. 5, the assembly 500 may comprise a sealing member 522 (as described earlier). The sealing member 522 can be configured to seal the assembly 500 with respect to the skin of the subject. For example, in embodiments such as that illustrated in FIG. 5 involving a coupling medium 514, the sealing member 522 can be configured to seal the second surface 510 of the sensor unit 501 and the coupling medium 514 with respect to the skin of the subject. That is, the sealing member 522 can be configured to seal the coupling medium 514 between the second surface 510 of the sensor unit 501 and the skin of the subject. This prevents the coupling medium 514 being in direct contact with air and avoids evaporation. In this way, dehydration of the coupling medium 514 is prevented and coupling of the sensor unit 501 (and thus the sensor 502) can be maintained for longer periods of time.

In the example embodiment illustrated in FIG. 5, the assembly 500 comprises an adhesive member 512. The adhesive member 512 may extend around a periphery of the assembly 500, e.g. at least a part of the periphery or the entire periphery of the assembly 500. The adhesive member 512 may be configured to adhere (or fix) the assembly 500 to the skin of the subject. More specifically, in the example embodiment illustrated in FIG. 5, the adhesive member 512 can be configured to adhere (or fix) the at least one resilient member 508 to the skin of the subject.

In some embodiments, such as that illustrated in FIG. 5, the adhesive member 512 can comprise a first protector 520

(as described earlier) covering an outer portion of the adhesive member 512 around the perimeter of the adhesive member 512. Although not illustrated in FIG. 5, in some embodiments, the adhesive member 512 can alternatively or additionally comprise a second protector (as described earlier) covering an inner portion of the adhesive member 512. In some embodiments, the first protector 520 and/or the second protector may be removable. For example, at least the second protector may be removable according to some embodiments.

The coupling medium 114, 214, 514 can be an acoustic coupling medium optimally design for an acoustic wave transmission, when the sensor unit 101, 201, 501 is an ultrasound based sensor. The coupling medium might be formed as an integral part of the sensor unit or as a separate element of the assembly as illustrated in FIG. 5, wherein the coupling medium 514 is attached to the part 504. This part 504 of the assembly 500 forms a cavity for receiving the sensor unit 501, wherein the sensor's second surface 510 enables a collection of the sensor signal from the body via the coupling medium 514, which is located opposite to the opening of the cavity part 504. Once the sensor unit is received by the assembly (via the opening) the outer edge of the cavity arranged to secure the sensor unit to the assembly at another surface location (the first surface 506).

There is a physical distance between the securing contact of the assembly with the sensor unit 501 at the first surface 506 of the sensor unit and the location the resilient member 508 extending from the outer portion of the assembly part 504. The part of the assembly configured to contact with the first surface of the sensor unit is located at larger distance from the skin of the subject (once sensor unit is mounted in the assembly) compared to the location of the resilient member, wherein it is arranged to extend from an outer portion of the part and configured to bias the second surface of the sensor unit against the skin of the subject. This embodiment allows accommodating more varieties of the sensor unit designs (for example, larger sensor units, additional hardware of which enables local sensor functionalities) with still precise control of such a sensor's contact with the subject's skin. Having the resilient member 508 extending from the assembly part at the location in a closed proximity to the coupling medium 514 enables having a better control over the correction of the variation in medium's thickness during an extended period of time. While having the part of the assembly configured to contact with the first surface of the sensor unit at a further distance from the coupling medium 514, thereby encapsulating the entire sensor unit, allows assuring an improved contact of the sensor unit, when in use, with the subject irrespective of the sensor unit's dimensions.

The presented herein assembly enables a medical practitioner to reuse a usually more expansive sensor unit in several medical workflows by simply snapping the sensor unit 101, 201, 301, 401, 501 to the assembly and applying this coupled arrangement to the body. This provides a more sustainable solution for a medical sensor, wherein the assembly 100, 200, 300, 400, 500, which may also include the medium coupling element, can be disposed after a single use, while the sensor unit 101, 201, 301, 401, 501 can be reused a plurality of times. For an ultrasound monitoring application assuring a good acoustic contact between the subject's skin and the ultrasound based sensor unit might be of high importance for providing a good quality sensor signal (ultrasound derived). The presented herein invention with the resilient member's arrangement allows assuring a collection of the high quality sensor signal for an extended period of time.

Although some examples of an assembly have been described with reference to the figures, it will be understood that any of those assemblies may comprise alternative or additional components to those described. Also, each of the features described herein may apply to any of the example assemblies and a person skilled in the art will appreciate that other examples are possible.

There is thus provided herein an improved assembly 100, 200, 300, 400, 500 for mounting a sensor on the skin of a subject, which addresses the limitations associated with the existing techniques. By preloading at least one resilient member 108, 208, 308, 408, 508 in the manner described herein, the assembly 100, 200, 300, 400, 500 can maintain contact with the skin of the subject. This is possible even where geometric changes occur to the skin of the subject. Also, the contact with the skin can be maintained over an extended period of time. The force that the at least one resilient member 108, 208, 308, 408, 508 described herein is able to maintain is well-defined. The force need only be small, which prevents skin irritation.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An assembly for mounting a sensor on the skin of a subject, the assembly comprising:
   a part configured to contact with a first surface of a sensor unit comprising the sensor when the sensor unit is mounted in the assembly; and at least one resilient member extending from an outer portion of the part and configured to bias a second surface of the sensor unit against the skin of the subject when the sensor unit is mounted in the assembly;
   wherein the at least one resilient member extends around a perimeter of the outer portion of the part and comprises at least one elongate aperture;
   wherein the at least one elongate aperture is configured to widen when the assembly is attached to the skin of the subject;
   wherein the resilient member comprises a plurality of ribs extending around the perimeter of the outer portion of the part and defining the at least one elongate aperture;
   wherein at least one of the plurality of ribs is coupled along a section of its length to the perimeter of the outer portion of the part to form an H-shaped flexure; and
   wherein at least one of the plurality of ribs is, for forming an H-shaped flexure, configured to be attached to at least one other rib that is configured to be attached to the skin of the object.

2. The assembly as claimed in claim 1, further comprising:
   an adhesive member extending around a periphery of the assembly and configured to adhere the assembly to the skin of the subject.

3. The assembly as claimed in claim 2, wherein:
   the adhesive member is configured to adhere the at least one resilient member to the skin of the subject.

4. The assembly as claimed in claim 2, wherein:
   the adhesive member comprises:
      a first protector covering an outer portion of the adhesive member around the perimeter of the adhesive member; and
      a second protector covering an inner portion of the adhesive member, wherein at least the second protector is removable.

5. The assembly as claimed in claim 1, further comprising:
   a sealing member configured to seal the assembly with respect to the skin of the subject.

6. The assembly as claimed in claim 1, wherein the sensor comprises an ultrasound transducer.

7. The assembly as claimed in claim 6, wherein:
   the at least one resilient member is configured to bias the second surface of the sensor unit indirectly against the skin of the subject via an acoustic coupling medium.

* * * * *